United States Patent
Taylor

(10) Patent No.: US 6,990,850 B2
(45) Date of Patent: Jan. 31, 2006

(54) CURTAIN COATER RHEOLOGY MANAGEMENT

(76) Inventor: John A. Taylor, 12 Park Ave., Pompton Plains, NJ (US) 07444

( * ) Notice: Subject to any disclaimer, the term of this patent is extended or adjusted under 35 U.S.C. 154(b) by 89 days.

(21) Appl. No.: 10/662,666

(22) Filed: Sep. 15, 2003

(65) Prior Publication Data

US 2005/0056084 A1 Mar. 17, 2005

(51) Int. Cl.
*G01N 11/08* (2006.01)

(52) U.S. Cl. .................. 73/54.06; 73/54.06; 73/54.05; 73/40.7

(58) Field of Classification Search ............... 73/54.05, 73/54.06, 40.7
See application file for complete search history.

(56) References Cited

U.S. PATENT DOCUMENTS

| | | | | |
|---|---|---|---|---|
| 3,952,577 A | * | 4/1976 | Hayes et al. ................ | 73/54.04 |
| 4,627,271 A | * | 12/1986 | Abbott et al. ............... | 73/54.06 |
| 4,793,174 A | * | 12/1988 | Yau ............................ | 73/54.04 |
| 4,893,500 A | * | 1/1990 | Fink-Jensen ................ | 73/54.37 |
| 5,097,005 A | * | 3/1992 | Tietz .......................... | 528/272 |
| 6,470,736 B2 | * | 10/2002 | Price .......................... | 73/54.04 |
| 6,701,778 B2 | * | 3/2004 | Taylor ........................ | 73/64.48 |

* cited by examiner

*Primary Examiner*—Hezron Williams
*Assistant Examiner*—André K. Jackson
(74) *Attorney, Agent, or Firm*—Notaro&Michalos PC

(57) ABSTRACT

A method and apparatus for accurately determining the rheology of a coating fluid and using this information to design application equipment and formulations, particularly for non-Newtonian fluids, including measuring the entrance transition effects for the fluid at process shear rates and time frames, and detecting to presence of dilatant flow. A device for measuring these transition effects has a pressure source for the fluid and connector for a selected capillary tube. The fluid is introduced to the capillary and a pre-determined shear rate and flow rate are achieved. The resulting back pressure in the container is measured. The test parameters are changed to obtain the separate transition effect measurements to correspond to process conditions.

10 Claims, 2 Drawing Sheets

CURTAIN COATER RHEOLOGY MANAGEMENT

FIELD AND BACKGROUND OF THE INVENTION

The present invention relates generally to the field of rheology measurement for paints, inks, and coatings, and in particular to a new and useful device and method for measuring the transition or force to achieve a shear rate to more accurately determine the rheology of a given coating and use this force to forecast the results of the various application processes, to make better applicator designs, and to make improved formulations.

Coatings and surface treatments are commonly applied in industrial processes for reasons including merely changing the outward appearance of a product, protecting product surfaces from corrosion, weather or other environmental conditions, making the surface receptive to ink, creating liquid or gas barriers, creating a non-stick surface, and making a surface more or less adhesive, to name some. Several application processes and devices are known for applying these coatings, including sprayers, brushes, fan coaters, flow coaters, curtain coaters, roll coaters, Meyer rod coaters, Gravure coaters, blade coaters, air knife coaters, and meniscus coaters, among others.

It is well understood in the art that for any of these coaters to work properly, the rheology of the applied coating must be within a particular range, depending on the device and process conditions such as pick-up and speed. Accurate determination of coating fluid rheology is important to ensuring good and consistent quality coatings. For example, consistency is desirable for products coated with different batches of coating fluid on an assembly line. If the coating fluid does not have the proper rheology for the application, a poor quality coating will result.

Many times, the expense of the product and coating materials make errors in the rheology of the coating fluid very costly. Often, the only way to find the rheology of a coating is to run many test coatings to find one which works well for a particular application. But, the use of coating fluid samples and substrates in trial-and-error analysis becomes costly very quickly, due to time and materials wasted.

And, the inability to accurately predict the rheology of coating fluids is so deficient that coating dies cannot be made to run multiple coatings. That is, a single die is typically designed to run a specific coating composition and it is very difficult to make a different composition run well through the same die. The distribution pressure losses compared to the die lip exiting flow losses vary enough between formulations that operations resort to using a number of dies to make different grades for the same coating.

Difficulties in accurately predicting process results from rheology measurements for a coating fluid arise from the fact that substantially all paints, sealers, protective coatings, etc., exhibit non-Newtonian behavior. Thus, in order to accurately predict the process a particular application, the measurement must mimic the application process conditions as much as possible. In particular, it is necessary to duplicate the intensity and duration of shear rate, shape of the flow field, and time for accurate viscosity or fluid friction measurements to model the process. All coating processes have a region with an extensional flow field of a short duration, so that a measurement intended to predict the fluid performance in a process must do the same.

Transition or entrance effects can be generally defined as the effect on a fluid as it passes between two regions of differing areas or different shear rates. For example, when a fluid enters a tube or channel, or at a point where the same tube or channel tapers wider or narrower. Viscosity measurements generally discard or effectively ignore transition effects of a fluid entering the test flow field. Reynold's work on laminar flows has demonstrated that between 10 and 20 pipe diameters displacement are needed after entering a pipe for laminar flow to develop.

Similarly, U.S. Pat. No. 3,071,001 states that it is established a non-linear pressure drop occurs at the pipe transition which is related to the density times the square of velocity, or the velocity head of the fluid. For non-Newtonian fluids, however, we have a different finding.

Many viscometers elect to minimize the transition effects. They either wait for the transition effect to pass before making any measurements, or they subtract a value related to the velocity head. For example, U.S. Pat. No. 6,470,736 teaches that the transition flow effect and Reynold's number should be minimized so as to allow interpretation of flow rate by the Poiseuille equation. This value is simply the pressure drop through a test pipe under steady state flow.

Viscometers which minimize or eliminate the transition effects are useful and effective for measuring the resistance of an equilibrium process like the flow through a pipe. And, they are helpful and correlate to some extent with process conditions within a narrow range of chemistries. But, generally, they are ineffective at predicting process results over a broad range of fluid chemistries using a single predictive model.

Some capillary viscometers presently pass over the transition effect by taking data only at a point after the transition effect has occurred, so that it is small (near zero) compared to the equilibrium viscous force. Other capillary viscometer measurements subtract out the force needed to reach the measured shear rate. They measure this force with a standard fluid—typically water—and use this value for all fluids tested. But, simply subtracting the transition or entrance force value of one fluid type from all fluid measurements will result in error because the actual force varies with each fluid, especially for viscous non-Newtonian fluids. So existing capillary viscometers either ignore or improperly consider the actual transition shear force.

While most viscometers minimize the transition effect in the reported reading, some do not. Such viscometers are taught in several patents, including U.S. Pat. No. 4,449,394, which has a short capillary tube at the bottom of a cup for receiving the fluid under test. The height of the fluid provides the pressure source. However, this viscometer does not match the process conditions and does not forecast process results over a broad range of fluid types. It operates at a declining shear rate. As the fluid level in the cup drops, the shear reduces to near zero, until the fluid flow stops. This viscometer cannot be used to measure the resistance to flow at specific shear rates, and only works well at low shear rates since it is not pressurized beyond the inherent fluid pressure. This viscometer has the effect of averaging out the shear force versus time as well, so that it measures an average viscosity over an average shear rate. And, process rates of 300,000/second or higher are not obtainable.

Another capillary viscometer is taught by U.S. Pat. No. 4,793,174 in which fluid flow through a capillary tube is started at a low pressure and then the pressure is suddenly increased. The resulting flow increase is recorded as a function of time. The capillary tube is significantly longer than 20 pipe diameters, so that the transition effect is essentially eliminated at the measurement point. The transition effect is lost in the average with the equilibrium viscosity through the tube. The length of the tube dilutes the initial shear force, while the overall flow does not have a constant shear rate.

The viscometer of U.S. Pat. No. 3,952,577 includes a plurality of pressure sensors along the flow path. The flow path is a rectangular channel of decreasing cross-sectional area. The decreasing size of the channel necessarily prevents the flow from having a constant shear rate. The viscometer is provided for use with laminar flows only.

Another tool which is useful but still fails to account for transition effects is an oscillating viscometer. This viscometer begins motion in one direction and then reverses to measure the elasticity of a fluid. The viscometer is experiencing the force to initiate flow, but measurement is not taken until after several oscillations, and the force to destroy initial gel structure of the fluid is not lost.

Concentric cylinder viscometers measure the force after the flow establishes a fully developed velocity gradient even when the velocity is steadily increased. This measurement is commonly referred to as a rheogram. One tool which can plot shear force versus time after a change in shear rate to measure the energy to "beat out" a coating is known as the Haake rheometer. But, this device fails to duplicate all coating application processes as it has a longer than realistic process duration, and it is not an extensional flow field.

None of the existing viscometers measures the transition effects accurately at the process conditions that correspond to the various coating and paint application processes.

It has been discovered that the transition force can vary greatly between fluids, and therefore, this force needs to be measured in each case. Thus, a rheology measurement device and method for accurately determining and accounting for transition effects of fluids is still needed.

SUMMARY OF THE INVENTION

It is therefore an object of the present invention to provide a rheology measurement device which accounts for the transition shear force of fluids used in coating, printing, and painting applications.

A further object of the invention is to provide a method of measuring non-Newtonian transition shear force of a coating, ink, or paint fluid to accurately determine rheology of the fluid.

It is a further object of this invention to provide a method of adjusting all fluid formulations to run with an application die with good cross machine profile characteristics.

Accordingly, a method for measuring the non-laminar transition effect of a fluid in a capillary tube is provided in which the force to break down the chemical structure in a fluid under shear to initiate flow is measured. In most cases, when a liquid such as a coating liquid, begins to flow through a region of smaller diameter, a rapid pressure drop is exhibited, followed by a constant slope pressure decrease. The present method measures and accounts for the rapid pressure drop which is ignored or eliminated by other measurements. The rapid pressure drop, corresponding to the entrance effect, has been found to be significant to predicting the rheology of non-Newtonian fluids in particular.

The measurement is obtained by first establishing a flow of the coating fluid under test into a capillary tube from a fluid source. The fluid is caused to flow at a flow rate giving a pre-determined, selected shear rate. The flow rate can be set with a pump or other mechanism for varying the pressure on the fluid. When the flow rate is achieved, the pressure of the fluid at the inlet to the capillary tube is measured. The transition shear pressure $P_{tr}$ is the total pressure minus the velocity head. The transition shear force $F_{tr}$ is related to the shear pressure as a function of the cross sectional area of the capillary tube and the area of the capillary tube walls.

The relationship of flow rate to shear rate at the walls of the capillary is function of the power law, m, of the fluid. The shear rate is a multiple of the velocity divided by the radius of the capillary. The transition shear force has been correlated to a variety of process conditions. Using the method of the invention, the shear force measured should duplicate that of the process condition under consideration. Using these relationships, the shear characteristics for the fluid under test can be determined. And, therefore, the rheology of the fluid is determinable more accurately than when the entrance effects are ignored or eliminated.

A testing apparatus for measuring the pressure of a fluid under test according to the inventive method has a container for a fluid source, a pump for pressurizing the fluid source, a pressure measurement gauge and a capillary tube connected with the fluid source. The pressure gauge is connected to the container to measure the pressure generated by the fluid as it attempts to flow through the capillary tube from the container. The pump or other similar mechanism is used to pressurize the fluid under test sufficiently to cause a desired flow and shear rate.

The testing apparatus preferably includes several different capillary tubes which are each connectable to an outlet of the container. The provision of many different capillary tubes of different diameters and lengths permits measuring the fluid rheology for different fluids and process conditions which may be experienced in coating applications.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
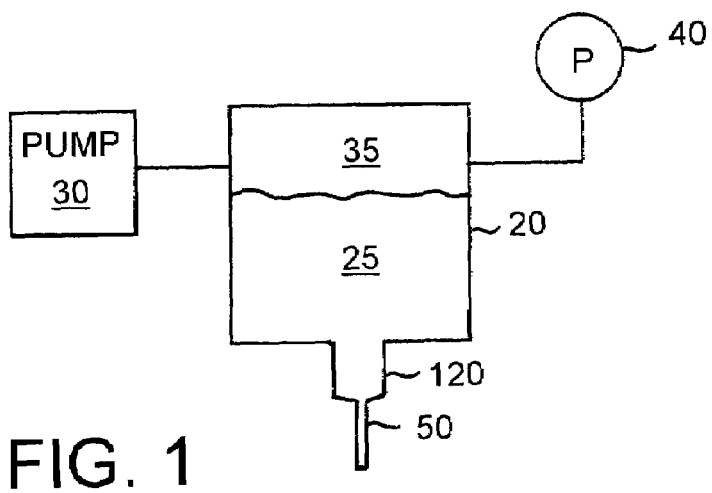
FIG. 1 is a schematic diagram of a testing apparatus of the invention.

The following principles and relationships of fluid rheology form the basis of the invention and are useful to understanding the measurement method and apparatus of the invention.

It has been found in curtain coating applications that the transition effect, or pressure loss, in the first 6 to 10 pipe diameters varies greatly with the composition or chemistry of non-Newtonian fluids. And, the relationship between pressure loss and flow rate can have power laws with velocity ranging from zero, independent of flow, to at least 2.5. This is significantly different because, usually, the reported value of one velocity head is related to the square of the fluid flow.

In high viscosity fluids, the transition effect can easily be 8 or 10 velocity heads. The transition effect for non-Newtonian fluids is actually a measure of the force to break down or "beat out" any chemical structure in the fluid as it accelerates from a low shear rate to a higher shear rate. These forces can overwhelm the kinematics or the velocity head of transition.

Further, the transition effect, measured as a shear force, correlates to the application processes when the shear rate of the measurement corresponds to the shear rate present in the application process. This correlation holds for all types of fluids regardless of the source of viscous friction: dissolved polymers, particles, latex emulsions, 100% solids coatings, oils, or neat polymers. The universal aspect of this correlation is very economically important as it eliminates the need for process tests with new formulations.

The transition shear pressure $P_{tr}$ is the total pressure minus the velocity head. The transition shear force $F_{tr}$ is related to the shear pressure as follows:

$$F_{tr} = P_{tr} * A_c / A_w$$

where, $A_c$ is the cross sectional area of the capillary, and $A_w$ is the area of the capillary walls.

The relationship of flow rate Q to shear rate (SR) at the walls of a capillary is function of the power law of the fluid:

$$SR = (3+m)Q/\pi R^3$$

where, m is the observed exponent of $F_{tr}$ as function of $(Q/\pi R^3)$, Q is the flow rate, and R is the radius of the capillary tube.

The transition shear force, $F_{2000}$, with surface tension, and as measured in co-pending application Ser. No. 10/131,966 filed Apr. 25, 2002, the entirety of which is hereby incorporated herein, correlates very well with the lower coat weight limit for the curtain coating process. It was found that the lower coat weight limit can be predicted by measuring a property called "stretch" and the falling velocity. An elastic flow test is also disclosed.

And, the same designs used to simulate the maximum shear rate of the process will detect dilatant effects. Dilatant fluids will not flow out evenly and leave a blotchy appearance if used in an application process. Dilatant behavior is exhibited, for example, when a fluid experiences a sharp contraction from a capillary tube channel 0.25 inches in diameter to one 0.033 inches in diameter at high flow rates. If the tube plugs at the process shear rate, it indicates dilatant behavior.

Generally the presence of elastic or dilatant behavior prevent the good application of a fluid. These behaviors always arise when the solids level in the coating fluid is high enough. But, running coating fluids with high solids content is always desirable because such fluids reduce drying energy, space requirements, and equipment costs. Thus, running coating processes with fluids containing just below the problem level of solids is desirable. Elastic and dilatant behavior are process constraints that determine the upper solids level.

These rheology properties and others are measured using the device and method of the invention, as will now be described in greater detail. As used herein, shear forces are referred to a $F_x$ where X is the shear rate.

Referring now to the drawings, in which like reference numerals are used to refer to the same or similar elements, FIG. 1 shows a testing device 10 of the invention having a container 20 with a liquid source 25 and air 35 under pressure from a pump 30 or other similar mechanism. The liquid source 25 is a coating fluid under test. A pressure gauge 40 is connected to the container 20 for measuring back pressure in the container 20. An outlet 120 is provided at the lower end of the container and has an adapter 125 for receiving one of several capillary tubes 50. The pressure gauge 40 indicates the pressure needed to obtain a particular shear and flow rate through the capillary tube 50.

The capillary tubes 50 used with the testing device 10 have different lengths and inner diameters, and are selected depending on the particular transition effect value being measured. As used herein, diameter of a capillary tube refers to the inner diameter dimension of the capillary tube available for a coating liquid to pass through unless noted otherwise. Preferred sizes for the capillary tubes 50 used with the device 10 include capillaries with diameters between 0.010 inches and 0.050 inches as a practical range and having lengths from 0.2 inches to 6 inches. Below 0.010 inches diameter, the capillary tubes plug too easily, and above 0.050 inches, the pressure difference becomes too small to measure accurately. Capillary diameters of between 0.020 inches and 0.033 inches are preferred. Several capillary tubes 50 are preferably provided for modeling a range of process conditions using the measurement device 10.

The size of the outlet 120 is preferably at least about 0.250 inches diameter, but may range from 1 inch to 0.100 inches. The outlet 120 length is sufficiently large that the transition effect exhibited by the liquid 25 entering the outlet 120 can be discounted, as the pressure loss is near zero, and so only the desired transition effect is measured. The outlet 120 may include a rapid fastener (not shown) for quickly changing the capillary tubes 50 for different tests. For example, a ring connector which seals the outlet 120 against a selected capillary tube 50 by tightening a threaded connection can be used.

In use, the testing device 10 is provided with an amount of a test fluid 25 in the container 20. Air 35 is pressurized to a desired level to produce a particular flow rate through outlet 120 and a selected capillary 50. Then, once the shear rate is obtained in the flow through the capillary tube 50, the pressure gauge 40 is read to determine the pressure in PSI needed to produce the selected conditions.

Examples of coating processes which can be modeled using the testing device 10 of the invention, preferred shear rates, capillary tube 50 dimensions and approximate flow rates for each process are identified in the following table:

| Process | Shear Rate (1/sec) | Preferred Tube Diameter (inches) | Preferred Flow Rate (cc/min) |
|---|---|---|---|
| Meyer Rod | 62,000 | 0.033 | 220 |
| Curtain Contraction | 2,000 | 0.020 | 1.58 |
| Falling Curtain | 20,000 | 0.020 | 15.8 |
| Curtain Landing | 300,000 | 0.033 | 1066 |
| Curtain Landing | 300,000 | 0.030 | 801 |

The values set forth in the table above are not intended to be limiting in that the tube diameters and flow rates may be changed to suit particular situations. For example, any capillary tube diameter within the acceptable range may be used for each test. Similarly, the flow rates will depend on the particular fluid under test and ability to easily modulate the pressure of air 35 with the pump 30. But, it has been found that the indicated diameter tubes produce good results at the indicated flow rates for each listed test. To provide the full range of shear rate measurements required—from 10/second to 1,000,000/second—the testing device 10 for measuring the various $F_x$ values must have different diameter capillary tubes 50 for connecting with a pressurized source of a liquid 25 to be measured.

The transition shear force has been correlated to a variety of process conditions. The shear force measured should duplicate the process condition under consideration.

With the discovery of the correct measurement of the transition shear force, the lower coat weight limit can also be predicted from the surface tension of the water phase and $F_{2000}$. For example, FIG. 2 demonstrates that, theoretically, this force should be close to the yield point as it represents the viscous resistance to a stream pulling into a drop—a process that incurs low shear. Increasing this resistance allows lower curtain flow rates as surface tension cannot pull the curtain up fast enough.

In a method for determining the rheology of a coating fluid, the device 10 is used to take several measurements for a given liquid 25 corresponding to transition effects typically experienced in different situations in a coating process. The measurements are combined with indications of elastic and dilatant flow properties to accurately model the rheology of a given coating fluid. Examples of useful measurements are given below.

The method includes selecting and connecting a capillary tube 50 to the testing device 10, loading a coating fluid for testing into the device 10, pressurizing the fluid to generate a predetermined flow rate to produce a desired shear rate, and measuring the pressure with gauge 40 when the selected shear rate is obtained.

In the case of curtain coating, once the elastic and dilatant limit has been established, $F_{2000}$ and the surface tension determine the lower coat weight speed operating window as previously described. The measurement is preferably taken using a 0.020 inch diameter tube 0.25 inches long. $F_{2000}$ is a low shear force that retards the formation of drops in a falling curtain. As the value of $F_{2000}$ increases, the curtain velocity, thereby allowing a reduction in flow rate, while maintaining curtain momentum. For the curtain to remain stable, the momentum must exceed the surface tension. That is, the curtain must have a Weber number, We, greater than 1, where We is the momentum divided by surface tension, or:

$$QV/\Gamma$$

where, Q is the flow rate, V is the falling velocity, and $\Gamma$ is the surface tension.

Figure 2:
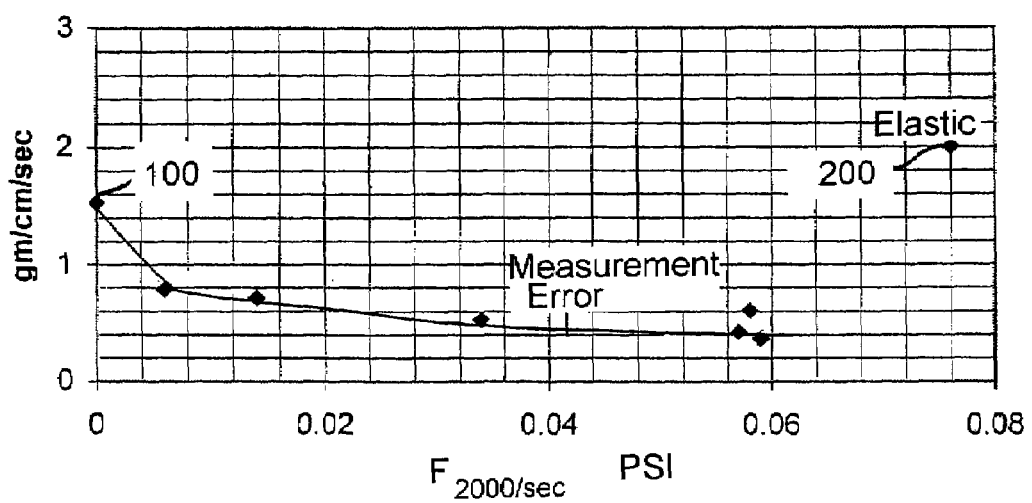
FIG. 2 is a chart illustrating the pinhole limit for 10.9 dyne/cm water for force applied at a shear rate of 2,000/sec versus flow rate in gm/cm/sec.

FIG. 2 graphically illustrates the minimum die flow to form a curtain and land without pinholes against shear force in PSI (pounds per square inch) at a shear rate of 2,000/sec. The point 100 on the vertical axis represents water and a surfactant. Water measures zero on the scale illustrated. Normally with previously reported technology, curtain coating processes require a formulation to have a flow rate preferably greater than 1 gm/cm/sec, and even more preferably, greater than 0.8 gm/cm/sec.

The $F_{2000}$ measurement permits rapid screening of different formulations for minimum flow rate. Use of the $F_{2000}$ measurement, for example, has permitted discovery of certain coating formulations which allow a minimum flow of 0.4 gm/cm/sec without creating pinholes. Generally, as the concentration of a rheology modifier increases, the shear force exhibited by the resulting coating fluid increases. Many known rheology modifiers become elastic around 0.015 PSI. At the elastic limit, the minimum flow to form a curtain decreases, but the flow rate to avoid pinhole formation increases, as illustrated by point 200 in the graph of FIG. 2.

A second application of the method, in the case of curtain coating, is to determine the upper coat weight limit or puddling limit. The puddling limit can be forecast from the surface tension, $F_{2000}$, and $F_{500k}$. The puddling limit is the maximum coating fluid flow rate that the coated sheet will carry away in an even layer. A flow rate greater than the puddling limit causes a heel to build up behind the curtain until it becomes unstable.

Figure 3:
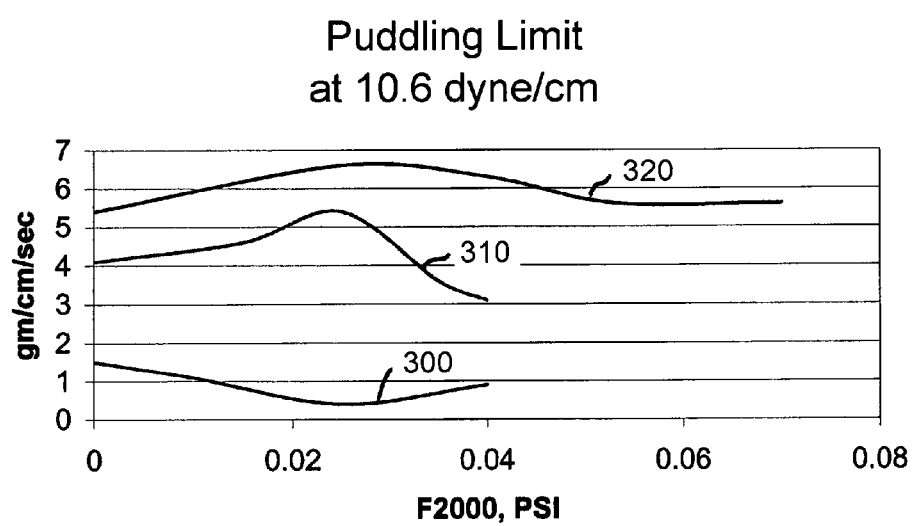
FIG. 3 is a graph showing upper coat weight limits for a fluid flowing at 500 feet/minute with a 10.6 dyne/cm surface tension, expressed in gm/cm of width/second as a function of $F_{2000}$ and $F_{500k}$.

FIG. 3 illustrates the puddling limit for a fluid in which $F_{500k}$ is held constant at three values, while $F_{2000}$ in PSI is plotted versus flow. The three curves 300, 310, 320, represent $F_{500k}$ values of 0, 1 and 2, respectively, for a coating liquid composed of 50% solids. The shear rate in the landing zone during a coating process will vary greatly with speed and the coating thickness. The shear rate may range from 50,000/sec to 1,400,000/sec. It has been found that measuring $F_{500k}$, the transition shear force at 500,000/sec, gives a good correlation. Higher $F_{500k}$ values can impart more horizontal force into the coating to make it accelerate and go with the web.

The $F_{500k}$ measurement is preferably taken with device 10 using a capillary tube 50 with a diameter of 0.033 inches and 0.25 inches long. Air 35 in the container 20 is pressurized with pump 30 to produce a selected flow rate of the liquid 25. As with the measurement $F_{2000}$, while the pressure in the container 20 increases, the shear rate is monitored until it reaches 500,000/sec. When the 500,000/sec shear rate is reached, the pressure on fluid 25 is read from gauge 40. The back pressure indicated on gauge 40 shows the pressure required to create a shear rate of 500,000/sec in the flowing liquid 25 through the selected capillary tube 50.

Since the $F_{2000}$ and $F_{500k}$ measurements account for transition effects on the liquid 25, the rheology model of the coating liquid 25 is more accurate than other models, and the coat-weight-speed-operating window for the coating liquid 25 is more accurately predicted. The increased accuracy of the model prediction reduces the effort to produce good quality, consistent coating formulations.

For example, once a base formulation is developed, the fluid properties to adjust the flow and make it runnable can be adjusted with between 2–10 coating batches of 500 cc each and testing with the testing device 10 and method to evaluate the rheology. This can result in a time savings of days and weeks over current processes for evaluating coating fluids. Further, pilot work to make market samples can be eliminated, as actual product can be produced on the commercial machines for salespeople to use to show customers. This efficiency can eliminate up to 6 months of manpower requirements.

A third application of the device 10 and method is for batch or continuous adjustment of viscosity to control the application thickness. This is useful in processes where the viscosity affects the wet thickness such as a Meyer rod coater, transfer roll coaters, reverse roll coaters, bar coaters, air knife, and blade coaters for example. In the case of a Meyer rod coater, $F_{63k}$ is the force of the fluid going over the rod. Controlling this force will control the wet pickup.

The advantage of this measurement taken with the device 10 and using the method over prior viscosity controllers is precision. The device 10 and method measure the actual process force and compensate for the random differences in viscosity caused by, for example, variation in the occupied volume of the fluid due to the hydraulic radius of an emulsion.

It is envisioned that a testing device 10 of the invention is connected with a coater, such as the Meyer rod coater, to monitor the coating fluid as it flows. A small portion of the process coating fluid may be diverted to the testing device 10 during the process for this purpose.

As yet another example, accurately measuring the resistance to flow exiting a set of die lips allows new formulations to be adjusted so they will run on an existing die designed for a different fluid. Coating dies are conventionally made with the die gap compensating for the cross machine pressure gradient from the cross machine flow resistance. Adjustable lip dies allow resetting the die for any coating, but this is not commonly done as it takes too much time. So, most coating dies have a good cross machine profile only for the original coating.

The measurement conditions will vary depending on the application, but typically, the die lip transition resistance force is measured using the device of the invention at shear rates of between 4,000/sec to 20,000/sec with a capillary tube having a diameter of about 0.020 inches and 0.25 inches long. In this case one needs to control the ratio of die lip shear force to the distribution cavity viscosity. For example, the ratio selected may be $F_{8000}$ to $V_{200}$, where $V_{200}$ is the viscosity at the distribution cavity shear rate. $V_{200}$ is measured with a conventional capillary that bypasses the transition resistance. Other force and viscosity ratios can be monitored and controlled instead, depending on the particular application.

Further, if a die with a 200/sec shear rate for distribution flow is used, it will be flow cleaning and have a higher pressure drop than the typical "large cavity" dies made today. Most dies use a large cavity to minimize the cross machine pressure drop and provide better profiles over a broader range of formulations. Having the ability to adjust the coating to the die permits the same and less expensive fixed slot die to be used with flow cleaning capabilities for any new formulation. This capability provides significant economic advantages when developing a mix of new products that are more closely matched to individual customer needs. The flow cleaning feature, previously not economically attainable, allows rapid product changes between coatings just by purging one coating out with the other.

While a specific embodiment of the invention has been shown and described in detail to illustrate the application of the principles of the invention, it will be understood that the invention may be embodied otherwise without departing from such principles.

What is claimed is:

1. A method for determining the rheology of a coating fluid, comprising:
    providing a testing device having a container, a pressure gauge connected to the container and a capillary tube at an outlet of the container, the capillary tube having a smaller diameter than the outlet;
    placing a sample of the coating fluid into the container of the testing device;
    selecting a coating fluid shear rate corresponding to a process shear rate of a coating application process;
    pressurizing the coating fluid sample to produce a predetermined flow rate through the capillary tube corresponding to the selected coating fluid shear rate;
    reading the back pressure on the coating fluid sample from the pressure gauge; and
    using the back pressure reading to determine an upper coat weight limit for the coating fluid.

2. A method according to claim 1, further comprising selecting the capillary tube from a plurality of capillary tubes each having different diameters.

3. A method according to claim 1, wherein the coating fluid shear rate is selected to be one of 2,000/sec, 20,000/sec, 62,000/sec, 63,000/sec, 300,000/sec, and 500,000/sec.

4. A method for determining the rheology of a coating fluid, comprising:
    providing a testing device having a container, a pressure gauge connected to the container and a capillary tube at an outlet of the container, the capillary tube having a smaller diameter than the outlet;
    placing a sample of the coating fluid into the container of the testing device;
    selecting a coating fluid shear rate corresponding to a process shear rate of a coating application process;
    pressurizing the coating fluid sample to produce a predetermined flow rate through the capillary tube corresponding to the selected coating fluid shear rate;
    reading the back pressure on the coating fluid sample from the pressure gauge; and
    using the back pressure reading to determine a pinhole limit for the coating fluid.

5. A method for determining and adjusting the rheology of a coating fluid used with a coating application die, wherein the coating application die is not designed specifically for the coating fluid, the method comprising:
    providing a testing device having a container, a pressure gauge connected to the container and a capillary tube at an outlet of the container, the capillary tube having a smaller diameter than the outlet;
    placing a sample of the coating fluid into the container of the testing device;
    selecting a coating fluid shear rate corresponding to a process shear rate of the coating application die;
    pressurizing the coating fluid sample to produce a predetermined flow rate through the capillary tube corresponding to the selected coating fluid shear rate;
    reading the back pressure on the coating fluid sample from the pressure gauge;
    determining if the rheology of the coating fluid is acceptable for the coating application die using the back pressure reading.

6. A method according to claim 5, further comprising adding a rheology modifier to the coating fluid to make a modified coating fluid if the coating fluid is not acceptable for the coating application die, followed by repeating the steps of placing a sample of the modified coating fluid through determining if the rheology of the modified coating fluid is acceptable.

7. A method according to claim 5, wherein the coating fluid shear rate is selected to be between about 2,000/second and 20,000/second.

8. A method according to claim 7, further comprising selecting the capillary tube from a plurality of capillary tubes each having different diameters.

9. A method according to claim 5, further comprising selecting the capillary tube from a plurality of capillary tubes each having different diameters.

10. A method according to claim 9, wherein the plurality of capillary tubes have diameters ranging from 0.010 inches to 0.050 inches.

* * * * *